(12) United States Patent
Stark et al.

(10) Patent No.: US 8,729,342 B2
(45) Date of Patent: May 20, 2014

(54) TREATMENT OF BANANA AND POTATO PLANTS WITH A NEW ANTIFUNGAL COMPOSITION

(75) Inventors: Jacobus Stark, Rotterdam (NL); Ferdinand Theodorus Jozef Van Rijn, Delft (NL); Wilhelmus Maria Van Der Krieken, Wageningen (NL); Lucas Henricus Stevens, Utrecht (NL)

(73) Assignees: DSM IP Assets B.V., Heerlen (NL); Ceradis B.V., Wageningen (NL)

( * ) Notice: Subject to any disclaimer, the term of this patent is extended or adjusted under 35 U.S.C. 154(b) by 364 days.

(21) Appl. No.: 12/808,425

(22) PCT Filed: Dec. 19, 2008

(86) PCT No.: PCT/EP2008/067975
§ 371 (c)(1),
(2), (4) Date: Sep. 28, 2010

(87) PCT Pub. No.: WO2009/077613
PCT Pub. Date: Jun. 25, 2009

(65) Prior Publication Data
US 2011/0047654 A1 Feb. 24, 2011

(30) Foreign Application Priority Data
Dec. 19, 2007 (EP) .................... 07123685

(51) Int. Cl.
*A01H 5/00* (2006.01)
*A01N 59/26* (2006.01)

(52) U.S. Cl.
USPC ............................ 800/298; 424/601; 424/605

(58) Field of Classification Search
USPC .................... 800/298; 424/601, 605
See application file for complete search history.

(56) References Cited

U.S. PATENT DOCUMENTS

| | | | |
|---|---|---|---|
| 4,148,891 A | 4/1979 | Smink | |
| 4,849,219 A * | 7/1989 | Staub et al. | 424/605 |
| 5,552,151 A | 9/1996 | Noordam et al. | |
| 5,597,598 A | 1/1997 | Van Rijn et al. | |
| 5,962,510 A | 10/1999 | De Haan et al. | |
| 6,150,143 A | 11/2000 | Raghoenath et al. | |
| 6,655,081 B1 | 12/2003 | Stark et al. | |
| 7,816,332 B2 | 10/2010 | Stark et al. | |
| 8,187,844 B2 | 5/2012 | Rijn et al. | |
| 2007/0264394 A1 | 11/2007 | Dutreux et al. | |
| 2008/0234210 A1 | 9/2008 | Rijn et al. | |
| 2010/0050299 A1 | 2/2010 | Stark et al. | |
| 2010/0050512 A1 | 3/2010 | Stark et al. | |
| 2010/0204168 A1 | 8/2010 | Haan et al. | |
| 2010/0234313 A1 | 9/2010 | Hee et al. | |
| 2010/0292315 A1 | 11/2010 | Van Hee et al. | |
| 2010/0297311 A1 | 11/2010 | Van Gurp et al. | |
| 2011/0059914 A1 | 3/2011 | Haan et al. | |
| 2012/0027905 A1 | 2/2012 | Stark et al. | |
| 2012/0052166 A1 | 3/2012 | Hooft et al. | |

FOREIGN PATENT DOCUMENTS

| | | |
|---|---|---|
| FR | 2 732 191 | 10/1996 |
| FR | 2 819 992 | 8/2002 |
| WO | 2005/074687 | 8/2005 |
| WO | WO 2006/136551 | * 12/2006 |
| WO | 2008/009657 | 1/2008 |

OTHER PUBLICATIONS

Written Opinion of the International Searching Authority for PCT/EP2008/067975, mailed May 26, 2009.
Brophy & Laing, Screening of fungicides for the control of downy mildew on container grown cabbage seedlings, Crop Protection, vol. 11 at p. 160-164 (Apr. 1992).
Reuveni et al., Controlling Downy Mildew (*Plasmopara viticola*) in Field-grown Grapevine with beta-Aminobutyric Acid (BABA), Phytoparasitica, vol. 29, Issue 2, pp. 125-133 (Jan. 23, 2001).
Li, et al., In Vitro Evaluation of Combination Antifungal Activity against *Fusarium* Species Isolated from Ocular Tissues of Keratomycosis Patients, American Journal of Opthamology, vol. 146, No. 5, 724-728 (Nov. 2008).
Rosato et al., In vitro synergic efficacy of the combination of Nystatin with the essential oils of *Origanum vulgare* and *Pelargonium graveolens* against some *Candida* species, Phytomedicine, vol. 16, No. 10, p. 972-975 (Oct. 2009).
Meletiadis et al., Triazole-Polyene Antagonism in Experimental Invasive Pulmonary Aspergillosis: In Vitro and In Vivo Correlation, Journal of Infectious Diseases, vol. 194, pp. 1008-1018 (Oct. 2006).
See Fungicide Resistance Action Committee, Mode of Action of Fungicides: FRAC classification on mode of action 2007, available at http://www.frac.info/frac/publication/anhang/FRAC_MoA_Poster_2007.pdf (last modified Feb. 12, 2007).
Mann, D.H., Romero R.A., Guzman, M., Sutton T.B., 2003, Black sigatoka: An increasing threat to banana cultivation, Plant Disease, 87(3),pp. 208-222.
Daly, A. and Walduck, G., 2006, *Fusarium* Wilt of Bananas (Panama Disease) *Fusarium oxysporum* f. sp. cubense. Agnote Northern Territory of Australia, 151, pp. 1-5.

(Continued)

*Primary Examiner* — Medina A Ibrahim
(74) *Attorney, Agent, or Firm* — Miles & Stockbridge, P.C.

(57) ABSTRACT

The present invention relates to the treatment of banana and potato plants with a composition containing natamycin and at least one phosphite containing compound.

17 Claims, No Drawings

(56) References Cited

OTHER PUBLICATIONS

Lassois, L., Jijakli, M. H., Chillet, M., de Lapeyre de Bellaire, L., 2010 Crown rot of banana: Preharvest factors involved in postharvest disease development and integrated control methods, Plant Disease, 94(6), pp. 648-658.

de Lapeyre de Bellaire, L., and Mourichon, X., 1997, The pattern of fungal contamination of the banana bunch during its development and potential influence on incidence of crown-rot and anthracnose diseases. Plant Pathology, 46 pp. 481-489.

Meredith, D.S., 1962, Some fungi on decaying banana leaves in Jamaica, Transactions of the British Mycological Society, 45, pp. 335-347.

Anthony, S., Abeywickrama, K., Dayananda, R., Wijeratnam S. W., and Arambewela, L. 2004. Fungal pathogens associated with banana fruit in Sri Lanka, and their treatment with essential oils, Mycopathologia, 157, pp. 91-97.

Wallbridge, A., 1981, Fungi associated with crown-rot disease of boxed bananas from the Windward Islands during a two year survey, Trans. Br. Mycol. Soc., 77, pp. 567-577.

Ploetz, R. C. 2000. Panama disease: A classic and destructive disease of banana. Online. Plant Health Progress doi:10.1094/PHP-2000-1204-01-HM.

Finlay, A.R., Brown, A.E., 1993, The relative importance of *Colletotrichum musae* as a crown rot pathogen on Windward Island bananas, Plant pathology, 42, pp. 67-74.

Udayanga, D., Manamgoda, D.S., Liu, X., Chukeatirote, E., Hyde, K.D., 2013, What are the common anthracnose pathogens of tropical fruits?, 61 (1), pp. 165-179.

Greene, G. L., Goos, R. D., 1963. Fungi associated with crown rot of boxed bananas. Phytopathology (Abstract).

\* cited by examiner

TREATMENT OF BANANA AND POTATO PLANTS WITH A NEW ANTIFUNGAL COMPOSITION

This application is the U.S. national phase of International Application No. PCT/EP2008/067975, filed 19 Dec. 2008, which designated the U.S. and claims priority to European Application No. 07123685.5, filed 19 Dec. 2007, the entire contents of each of which are hereby incorporated by reference.

FIELD OF THE INVENTION

The present invention discloses a new antimicrobial composition to prevent microbial spoilage of banana and potato crops. More in particular the present invention relates to a method for controlling *Mycosphaerella* and *Fusarium* growth on banana plants. *Mycosphaerella fijiensis* and *Fusarium oxysporum* f. sp. *cubense*, responsible for the so-called Black Sigatoka and Panama diseases, result in high losses and represent a real threat for the survival of banana varieties. The present invention also relates to a method for controlling *Alternaria* growth on potato plants.

BACKGROUND OF THE INVENTION

It is estimated that about 25% of the world crop production is lost due to microbial spoilage, of which spoilage by fungi is by far the most important cause. Not only from an economical point of view, but also from a humane point of view it is of great importance to prevent spoilage of food products. After all, in many parts of the world people suffer from hunger.

In that respect bananas are an important crop. Bananas are ranked fourth after rice, wheat and maize in human consumption. They are a valuable source of vitamin B6, vitamin C and potassium. The banana plant is an herb belonging to the genus *Musa* and is grown in more than hundred countries worldwide. Although being cultivated primarily for their fruit, they are to a lesser extent also used for the production of fiber and as ornamental plants.

*Fusarium* wilt, also called Panama disease, is caused by *Fusarium oxysporum*. It is the most widely spread disease of banana plants and, historically, the most important disease of bananas. Well-known epidemics devastated based export plantations up to the mid-1900s, and locally consumed cultivars continue to be affected worldwide. The introduction of resistant Cavendish cultivars in the tropics saved the international banana export trade industry during the 1960s. During the 1970's, however, Cavendish bananas succumbed to the disease in subtropical countries such as South Africa.

The disease has spread through plantations in Australia, South Africa and parts of Asia. It is only a matter of time before it reaches the hub of commercial production in Latin America and the Caribbean. No control strategy has been found to be effective in combating the disease, and most success has been achieved by preventative measures such as the isolation of infected plants and the planting of tissue culture plants in disease-free fields. Today, however, Panama disease is again threatening the world banana production.

Next to *Fusarium oxysporum*, the moulds *Mycosphaerella fijiensis* and *Mycosphaerella musicola* also cause diseases of banana leaves, the so-called Black and Yellow Sigatoka disease.

The production of bananas is most endangered by the Sigatoka leaf spot or the 'black leaf streak", caused by *Mycosphaerella fijiensis*. Black Sigatoka occurred for the first time about thirty years ago in some Central American countries. Within 10 years, Black Sigatoka became the predominant leaf disease in bananas with a self-accelerating spread to all important banana growing areas in Central and South America, Central and West Africa and wide areas of Asia.

The less dangerous Yellow Sigatoka disease occurs in banana plantations for several decades now. The disease attacks leaves during the entire growth period up to the time of harvesting. It initially causes spotting and blotching of the leaf surface that results in necrosis and withering of the leaf tissue. The course of the disease is usually slow, but the reduction of the active leaf surface leads to a weakening of the plant and an associated loss in yield. Because of its slow development, it was possible to control the disease by spraying the plants with mineral oil or with a mixture of mineral oil and fungicides.

Black Sigatoka differs from Yellow Sigatoka in its much more aggressive occurrence and in a disease cycle twice as rapid. The young leaves are infected even during formation and fade within 4-5 weeks. In addition to attacking all worldwide important banana table varieties, the disease also attacks the plantain fruit that constitutes the diet of the native population in wide areas of the tropical belt. Black Sigatoka has completely displaced Yellow Sigatoka in the most important banana growing areas.

The aggressive and epidemic occurrence of Black Sigatoka, especially in the tropical growing regions of America, Africa and Asia with their high rainfalls, leads to a rapid destruction of the banana plants. Infected leaves blacken, become necrotic and disintegrate. Planned production of bananas without appropriate protection against Black Sigatoka is no longer possible.

Spraying banana plants with chemicals is currently applied. The benzimidazole fungicides introduced at the beginning of the 1980's were very effective when sprayed at intervals of 2-3 weeks. However, due to the mechanism of action of this class of products and to their frequent application, Black Sigatoka developed an almost complete resistance to the benzimidazole deverivates within a few years.

For some years, triazole fungicides have been used with good success against Black Sigatoka. However, the number of spray applications per year had to be severely limited since their introduction on the market, in order to prevent the development of resistance. Despite this measure, a huge decrease in sensitivity has already been observed.

Further treatments have been suggested in e.g. WO 97/47202, wherein a fungicidal composition comprising natamycin and a fungal cell wall degrading enzyme and its use in the field of crop protection is described. In WO 2005/074687 an antifungal composition containing natamycin to prevent growth of pathogenic moulds on banana plants is described. In U.S. Pat. No. 4,148,891 an anti-fungal composition comprising natamycin, a lower alkanol and a lower alkanoic acid for the protection of agricultural products from mould growth is described.

It has been recognized that the world's most popular fruit and a basic staple food for hundreds of millions of people in the developing world—the banana—is under severe threat. *Mycosphaerella fijiensis* and *Fusarium oxysporum* f. sp. *cubense* can cause the extinction of the banana within 10 years. This would be a disaster to the 500 million Africans and Asians that are dependent on the production of bananas.

Producers, who can afford pesticides, spray the cultures up to 50 times a year. This is equivalent to ten times the average frequency applied in intensive agriculture plants of industrialized countries. The sprayings are not only expensive, making up a quarter of production costs, but present a serious risk to workers and a threat to the environment.

Next to the intensive use of pesticides, a much less aggressive method of control is the improvement of cultural methods. An early warning system has been developed to control Black Sigatoka. The system is based on weekly observations of symptoms on leaves of young plants followed by target fungicide applications within specific periods when disease severity is starting to increase and environmental conditions are favourable for disease development.

Cultural methods play an important role in reducing conditions for development of the disease. But, despite these control measures, the survival of edible banana species are seriously threatened by the Sigatoka and Panama diseases. No effective methods of preventing growth of fungi on banana plants, especially the growth of *Mycosphaerella fijiensis* and *Fusarium oxysporum* f. sp. *cubense*, without risk of development of resistance and without danger for the health of exposed persons and the environment, are presently known.

A further major plant disease problem for which conventional fungicide control is both intensive and a burden for the environment is early blight disease of potato. Potatoes are plants of the Solanaceae family. The potato is traditionally strongly associated with Europe, the United States of America and Russia because of its large role in the agricultural economy and history of these regions. But in recent decades, the greatest expansion of potato has been in Asia, where as of 2007 approximately eighty percent of the world potato crop is grown. Since the dissolution of the Soviet Union, China has become the world's largest potato producer, followed by India.

Potatoes are generally grown from the eyes of another potato and not from seed. Some commercial potato varieties even do not produce seeds at all and are propagated only from tuber pieces. These tubers or tuber pieces are called "seed potatoes".

Early blight disease is caused by the fungi *Alternaria solani* and *Alternaria alternate*. The disease is the major potato disease in the USA and constitutes an increasing problem in Europe. *Alternaria* produces small darkened lesions on the potato plants that spread into growing black spots of dead tissue, often killing most of the plant in the long run. Seeds infected with the disease may even damp off during germination. This disease can be prevented with some fungicides, including azoxystrobin. However, intensive use of fungicides has caused a widespread shift in *Alternaria* population towards species and strains that are resistant to the most commonly used products. The danger for the health of exposed persons and the environment is a further serious disadvantage of the currently used products.

Consequently, it can be concluded that there is a severe need for more effective, more environmental friendly, lower-toxicity and less harmful antimicrobial compounds/compositions, e.g. antifungal compounds/compositions, for the treatment of mould growth in and on banana and potato plants.

DESCRIPTION OF THE INVENTION

The present invention solves the problem by providing a new synergistic antimicrobial, e.g. antifungal, composition comprising a polyene antifungal agent and at least one phosphite containing compound and a process for the treatment of banana plants and other plantain plants as well as potato plants by applying the new composition to the plants. By applying the new antimicrobial composition fungal growth on or in banana and plantain plants and potato plants can be prevented. In other words, the new compositions of the invention protect the plants from fungal growth and/or from fungal infection and/or from fungal spoilage. The new compositions of the invention can also be used to treat banana and plantain plants that have been infected with a fungus such as e.g. *Mycosphaerella musicola, Mycosphaerella fijiensis* or *Fusarium oxysporum* or potato plants that have been infected with a fungus such as e.g. *Alternaria solani* or *Alternaria alternata*. By applying the compositions of the invention the disease development due to fungi on or in these plants can be slowed down, stopped or the plants may even be cured from the disease. The present invention offers a solution to protect banana and plantain plants from the devastating Sigatoka and Panama disease and potato plants from the serious early blight disease. According to the invention, banana and plantain plants and potato plants are treated with a composition of the invention effective to prevent or inhibit fungal growth, especially *Mycosphaerella fijiensis* and *Fusarium oxysporum* f. sp. *Cubense* and *Alternaria solani* and *Alternaria alternata*, respectively.

The composition can be advantageously applied on plants that comprise bananas or potatoes, but also on plants that do not contain any fruit/potato, e.g. because the fruit/potato has been harvested or because the plant has not grown any fruit/potato yet.

Unexpectedly, the present inventors have found that the protection of banana and plantain plants and potato plants against fungi is markedly enhanced when a polyene fungicide, e.g. natamycin, is combined with a natural crop protection compound belonging to the group of phosphites, e.g. $KH_2PO_3$ or $K_2HPO_3$ or a mixture of both phosphite salts, and the combination is applied to the plants. Phosphite containing compounds as used herein means compounds comprising a phosphite group, i.e. $PO_3$ (in the form of e.g. $H_2PO_3^-$, $HPO_3^{2-}$ or $PO_3^{3-}$) and includes compounds such as phosphorous acid and phosphonic acid as well as derivatives thereof such as esters and/or alkali metal or alkaline earth metal salts thereof. A composition comprising natamycin and phosphite and its use in crop protection has been disclosed in WO 2008/009657. However, WO 2008/009657 does not disclose the use of the composition in the treatment of banana, plantain and/or potato plants.

The compositions of the present invention therefore comprise a polyene fungicide and at least one phosphite containing compound. The ratio of phosphite to natamycin (in weight) in the compositions is in general between 2:1 to 500:1 (w/w), preferably between 3:1 to 300:1 (w/w) and more preferably between 5:1 to 200:1 (w/w). In an embodiment the compositions of the invention comprise 0.1 g or less lignosulphonate, more preferably 0.1 g or less polyphenol, per gram polyene fungicide. Preferably, they comprise 0.01 g or less lignosulphonate, more preferably 0.01 g or less polyphenol, per gram polyene fungicide. In particular, they are free of lignosulphonate and preferably free of polyphenol.

Suitable examples of polyene fungicides applied in the compositions of the invention are natamycin, nystatin, amphotericin B, aureofungin, filipin and lucensomycin. The preferred polyene fungicide is natamycin. In an embodiment the compositions may also contain two or more different polyene fungicides. It is to be understood that derivatives of polyene fungicides including, but not limited to, salts or solvates of polyene fungicides or modified forms of polyene fungicides may also be applied in the compositions of the invention. An example of a commercial product containing natamycin is the product with the brand name Delvocid®. Delvocid® is produced by DSM Food Specialties (The Netherlands) and contains 50% (w/w) natamycin. Said commercial products can be incorporated in the compositions of the invention. After many years of continuous use of natamycin, natamycin-resistant fungi have never been found. So, under normal conditions the compositions of the invention will protect banana and plantain plants and potato plants fully against fungal attack.

Suitable examples of phosphite containing compounds are phosphorous acid and its (alkali metal or alkaline earth metal) salts such as potassium phosphites e.g. $KH_2PO_3$ and $K_2HPO_3$, sodium phosphites and ammonium phosphites, and ($C_1$-$C_4$) alkyl esters of phosphorous acid and their salts such as aluminum ethyl phosphite (fosetyl-Al), calcium ethyl phosphite, magnesium isopropyl phosphite, magnesium isobutyl phosphite, magnesium sec-butyl phosphite and aluminum N-butyl phosphite. Of course, mixtures of phosphite containing compounds are also encompassed. A mixture of e.g. $KH_2PO_3$ and $K_2HPO_3$ can easily be obtained by e.g. adding KOH or $K_2CO_3$ to a final pH of 5.0-6.0 to a $KH_2PO_3$ solution. As indicated above, precursor-type compounds which in or on the plant are metabolized into phosphite compounds can also be included in the compositions of the present invention. Examples are phosphonates such as the fosetyl-aluminium complex. In or on e.g. a plant the ethyl phosphonate part of this molecule is metabolized into a phosphite. An example of such a compound in the commercial ethyl hydrogen phosphonate product called Aliette® (Bayer, Germany). In FR 2 819 992 a fungicidal composition based on potassium acid phosphite having a pH of less than 4 is disclosed. In FR 2 732 191 a phosphite composition for the treatment of cercosporiosis is disclosed.

Composition of the invention may have a pH of from 4 to 8, preferably of from 5 to 7. They may be solid, e.g. powder compositions, or may be liquid. Advantageously, they are liquids which can be applied by spraying of e.g. banana or potato plants. Other methods suitable for applying the compositions of the present invention in liquid form to the plants are also a part of the present invention. Spraying applications using automatic systems are known to reduce the labour costs and are cost-effective. Methods and equipment well-known to a person skilled in the art can be used for that purpose. The compositions according to the invention can be regularly sprayed on banana and plantain plants and potato plants, when the risk of infection is high. When the risk of infection is lower—for banana plants outside the rainy season—the spray intervals may be longer. The compositions according to the invention can even be sprayed preventively. Advantages of the compositions reside in e.g. the efficacy of the compositions even at low concentrations and the absence of development of microbial resistance to e.g. natamycin, even after frequent exposures. Furthermore, the compositions of the invention do not present any hazard for the health of exposed personnel and to the environment. They are therefore particularly suitable for a combined control strategy with improved culture measures.

In an embodiment banana and plantain plants and potato plants may be treated with a composition comprising a polyene antifungal, e.g. natamycin, followed by treatment with a composition comprising at least one phosphite containing compound or vice versa. In addition, banana and plantain plants and potato plants can be treated with other antifungal and/or antimicrobial compositions either prior to or after treatment of the plants with the compositions of the invention.

In a further embodiment banana and plantain plants and potato plants may be treated with a composition comprising at least one phosphite containing compound followed by post-harvest treatment of the bananas and potatoes with natamycin. Treatment of the plants and/or treatment of the bananas and/or potatoes may also be done with a composition according to the invention.

The compositions of the present invention also include concentrated stock suspensions/solutions and concentrated dry products such as e.g. powders, granulates and tablets. They can be used to prepare compositions for spraying of the plants.

A composition of the present invention will generally comprise 0.005 g/l to 100 g/l and preferably 0.01 g/l to 50 g/l of a polyene fungicide. Preferably, the amount is from 0.03 g/l to 3 g/l. Preferably, the polyene fungicide is natamycin. The amount of phosphite in the compositions of the invention is from 0.5 g/l to 1000 g/l, preferably from 1 g/l to 500 g/l and more preferably from 2 g/l to 200 g/l. A composition comprising e.g. potassium phosphite will generally comprise 0.5 g/l to 1000 g/l and preferably 1 g/l to 500 g/l potassium phosphite. More preferably, the amount of potassium phosphite is from 2 g/l to 200 g/l. According to the present invention also other phosphites may be used in equimolar amounts to the potassium phosphite. In an embodiment the concentration of the phosphite, i.e. $PO_3$ group, in the composition of the invention is between 1 and 1000 mM, preferably between 10 and 750 mM and more preferably between 25 and 500 mM.

In addition, the compositions of the invention may also contain at least one other antifungal compounds such as e.g. imazalil (Janssen Pharmaceutica NV, Belgium), thiabendazole (e.g. the commercial product TECTO® Flowable SC of Syngenta, USA), benomyl, captan (nonsystemic phthalimide fungicide), bitertanol (e.g. the commercial product Baycor®, Bayer crop protection), prochloraz (N-propyl-N-[2-(2,4,6-trichlorophenoxy)ethyl]imidazole-1-carboxamide) and formalin and commercial products known under the name Topsin® M (Cerexagri Inc, active ingredient thiofanaat-methyl), Jet-5® (Certis Europe BV, The Netherlands, active ingredients peracetic acid and hydrogenperoxide) and Shirlan® (Syngenta, Switserland, active ingredient fluazinam). Further suitable antifungal compounds can be found in Gewasbeschermingsgids 2006, Gids voor gewasbescherming in de land—en tuinbouw en het openbaar en particulier groen, Plantenziektenkundige Dienst, 2006, 560 pages, Paperback, Gewasbeschermingsgids—ISSN 1571-201X, Volume 18.

The composition of the invention may advantageously contain at least one sticking agent, which improves the sticking of the antifungal compound to the surface of e.g. the banana and plantain plants or potato plants. Examples of such sticking agents are latex based products like Prolong® (Holland Fyto B. V., The Netherlands) and Bond® (Loveland Industries Ltd), pinolene/terpene based products like Nu-Film® (Hygrotech Saad) and Spray-Fast® (Mandops) and long chain polysaccharides like xanthan gum, gellan gum and guar gum. Alternatively, the sticking agent may be a polymer or co-polymer from a type of polymer such as polyacrylate and polyethylene e.g. Neocryl® (DSM, The Netherlands). The composition of the invention may also comprise two or more different sticking agents.

For treating objects with a hydrophobic surface such as e.g. banana and plantain plants or potato plants, the addition of at least one surfactant may be of advantage. The optional addition of said compounds to the compositions of the invention is therefore also included in this invention. Examples of useful surfactants are anionic tensides such as sodium lauryl sulphate or polyethylene alkyl ethers or polyoxyethylethers, e.g. Tween® 60, 61 or 65. Other examples of useful surfactants are organo silicones, sulfosuccinates, alcohol ethoxylates, fatty acid ethoxylates, fatty acid propoxylates and the commercial product Zipper® (Asepta BV, The Netherlands). So, in a specific embodiment the compositions of the invention may further comprise additional compounds such as surfactants, sticking agents, suitable carriers and adjuvants ordinarily employed in formulation technology, including, but not limited to, mineral substances, solvents, dispersants, emulsifiers, wetting agents, stabilisers, antifoaming agents, buffering agents, UV-absorbers and antioxidants. In an embodiment the composition of the invention comprises a polyene fungicide (e.g. natamycin), a phosphite, a buffering agent (e.g. a carbonate containing salt, an acid or salt thereof), a dispersing agent (e.g. vinasse), a surfactant (e.g. emulsogen) and an anti-oxidant (e.g. ascorbic acid).

To improve the effectiveness and the practical use of the compositions of the present invention also compounds to combat insects, nematodes, mites and bacteria may be added to the antifungal composition. Examples of such compounds are Admire®(Bayer), formalin and Actellic® (Syngenta, Switzerland). These compounds may also of course be applied separately from the compositions of the invention.

Furthermore, the invention provides banana and plantain plants as well as potato plants treated with the compositions of the present invention. The treated plants may contain a composition of the invention, such as a coating comprising a composition of the invention. In an embodiment the treated plants comprise from 0.000001 to 200 mg/dm$^2$, preferably 0.00001 to 100 mg/dm$^2$, more preferably from 0.00005 to 10 mg/dm$^2$, natamycin on their surface. In a further embodiment they comprise from 0.001 to 1000 mg/dm$^2$, preferably 0.01 to 600 mg/dm$^2$, more preferably from 0.1 to 300 mg/dm$^2$ potassium phosphite on their surface. According to the present invention also other phosphite containing compounds may be used, therefore, the treated plants may comprise other phosphite containing compounds in equimolar amounts to the potassium phosphite on their surface. In case of banana and plantain plants the compositions can be applied on leaves, the main or upright stem (the so-called pseudostem), flowers, corms, offshoot of the plants, seeds or cultivars and even on bananas or plantains. In case of potato plants the compositions can be applied on leaves, flowers and the potato, to name just a few. So, these parts of the plants treated with a composition of the present invention are also included in the present invention.

EXAMPLES

Example 1

Treatment of Banana Plants Against Black Sigatoka Disease

The experimental design was a randomized complete block design with three treatments and an untreated control in three replications. Each plot contained 30 banana pseudostems. The plots were treated with composition 1, composition 2 or composition 3, the latter two containing only one of the active ingredients of composition 1 (see Table 1). Each composition was applied by spraying in a dosage of 20 l/hectare, using a knapsack manual sprayer and a knapsack engine mist blower. The pH of the compositions was 5.5. One plot was untreated (untreated control).

The plots were sprayed at an interval of 7 days. Disease rating was performed weekly during the treatment periods, using the Evolution Status Rating. This rating uses parameters including Incidence, Severity, YLS (youngest leaf spotted) and number of leaves at flowering (see Ordjeda, 1998). The period of application was 0-7 weeks after transplanting of the plants from the nursery to the plantation. Data were submitted to two-way Analysis of Variance and the Fisher Least Significant Difference test. Synergistic activity of the two active ingredients in composition 1 was tested in the Analysis of Variance model using the treatment interaction stratum (see Slinker, 1998).

The relative efficacy as shown in Table 2 was calculated by means of the following formula: ((value of evolution status of untreated control−value of evolution status of composition)/(value of evolution status of untreated control))*100.

The interaction coefficient as shown in Table 2 was calculated by means of the following formula: ((relative efficacy of combination natamycin+phosphite)/(relative efficacy of natamycin+relative efficacy of phosphite))*100. An interaction coefficient larger than 100 indicates synergy between the compounds. The interaction coefficient of the composition comprising natamycin and phosphite in the treatment of banana plants is 136.4.

The obtained results show that the compositions of the present invention protect banana plants from mould growth and further demonstrate that the compositions of the present invention show a synergistically enhanced activity compared to the activity of the active compounds when applied individually (see Table 2).

Example 2

Treatment of Potato Plants Against Early Blight Disease

The plot size was 5 m×3.75 m with a net plot for assessments of 4 m×2.25 m. The row spacing was 0.75 m. The potato variety used was Bintje. The potato plants were treated with composition 1, composition 2 or composition 3, the latter two each containing only one of the active ingredients of composition 1 (see Table 3). The pH of the compositions was 5.5. Furthermore, a plot was untreated (untreated control). Treatments were carried out in three replications. The applications were carried out with a 5-7 day interval. The treatment rates were equivalent to 300 l/hectare/spray. The equipment used to carry out the applications was a tractor mounted compressed air sprayer with a boom of 3.75 m carrying flat fan nozzles of type XR11003VS. Disease progress of *Alternaria* was rated once or twice a week. The percentage of the leaf area of the potato plants infected with *Alternaria* was estimated visually. The trial lasted the complete growing season of the potatoes, i.e. 1 May to 14 August (15 weeks). Data processing was as follows; the area under the disease progress curve was calculated by trapezoidal integration (see Campbell & Madden, 1990) and submitted to two-way Analysis of Variance and the Fisher Least Significant Difference test. Synergistic activity of the two active ingredients in composition 1 was tested in the Analysis of Variance model using the treatment interaction stratum (see Slinker, 1998).

The relative efficacy as shown in Table 4 was calculated by means of the following formula: ((value of area under disease curve of untreated control−value of area under disease curve of composition)/(value of area under disease curve of untreated control))*100.

The interaction coefficient as shown in Table 4 was calculated by means of the following formula: ((relative efficacy of combination natamycin+phosphite)/(relative efficacy of natamycin+relative efficacy of phosphite))*100. An interaction coefficient larger than 100 indicates synergy between the compounds. The interaction coefficient of the composition comprising natamycin and phosphite in the treatment of banana plants is 137.7.

The obtained results show that the compositions of the present invention protect potato plants from mould growth and further demonstrate that the compositions of the present invention show a synergistically enhanced activity compared to the activity of the active compounds when applied individually (see Table 4).

TABLE 1

Specification and dosage of ingredients per spray of compositions 1, 2 and 3 as used in the treatment of banana plants.

| | composition 1 | | composition 2 | | composition 3 | |
|---|---|---|---|---|---|---|
| | g/l | g/ha/spray | g/l | g/ha/spray | g/l | g/ha/spray |
| Natamycin | 0.5 | 10 | 0.5 | 10 | 0 | 0 |
| Potassium phosphite | 144 | 2880 | 0 | 0 | 144 | 2880 |
| Potassium carbonate (buffering agent) | 24 | 480 | 0 | 0 | 24 | 480 |
| Vinasse (Dispersing agent) | 60 | 1200 | 60 | 1200 | 60 | 1200 |
| Emulsogen (Surfactant) | 5 | 100 | 5 | 100 | 5 | 100 |
| Sodium citrate (buffering agent) | 40 | 800 | 10 | 200 | 40 | 800 |
| Citric acid (buffering agent) | 0 | 0 | 2.7 | 54 | 0 | 0 |
| Ascorbic acid (antioxidant) | 1.6 | 32 | 1.6 | 32 | 1.6 | 32 |

TABLE 2

Effect of compositions in the protection of banana plants from Black Sigatoka disease.

| Treatment | Evolution Status | Relative efficacy | Interaction coefficient |
|---|---|---|---|
| composition 1 | 20 | 60 | 136.4 |
| composition 2 | 41 | 18 | — |
| composition 3 | 37 | 26 | — |
| Untreated control | 50 | 0 | — |

TABLE 3

Specification and dosage of ingredients per spray of compositions 1, 2 and 3 as used in the treatment of potato plants.

| | composition 1 | | composition 2 | | composition 3 | |
|---|---|---|---|---|---|---|
| | g/l | g/ha/spray | g/l | g/ha/spray | g/l | g/ha/spray |
| Natamycin | 0.05 | 15 | 0.05 | 15 | 0 | 0 |
| Potassium phosphite | 14.4 | 4320 | 0 | 0 | 14.4 | 4320 |
| Potassium carbonate (buffering agent) | 2.4 | 720 | 0 | 0 | 2.4 | 720 |
| Vinasse (Dispersing agent) | 6.0 | 1800 | 6.0 | 1800 | 6.0 | 1800 |
| Emulsogen (Surfactant) | 0.5 | 150 | 0.5 | 150 | 0.5 | 150 |
| Sodium citrate (buffering agent) | 4.0 | 1200 | 1.0 | 300 | 4.0 | 1200 |
| Citric acid (buffering agent) | 0 | 0 | 0.27 | 81 | 0 | 0 |
| Ascorbic acid (antioxidant) | 0.16 | 48 | 0.16 | 48 | 0.16 | 48 |

TABLE 4

Effect of compositions in the protection of potato plants from Alternaria disease.

| Treatment | Area under the disease curve | Relative efficacy | Interaction coefficient |
|---|---|---|---|
| composition 1 | 112.2 | 43.3 | 137.7 |
| composition 2 | 168.0 | 15.2 | — |
| composition 3 | 165.7 | 16.3 | — |
| Untreated control | 198.0 | 0 | — |

REFERENCES

Campbell C L and Madden L V (1990), Introduction to Plant Disease Epidemiology. John Wiley & Sons. New York, Chichester, Brisbane, Toronto, Singapore, 532p.

Ordjeda G (1998), Inibap Technical Guidelines 3: Evaluation of *Musa* germplasm for resistance to Sigatoka diseases and *Fusarium* wilt. IPGRI International Plant Genetic Resources Institute, 62 pp.

Slinker B K (1998), The Statistics of Synergism. Journal of Mol. and Cell. Cardiology 30:723-731.

The invention claimed is:

1. A process for the treatment of banana, or plantain plant, or potato plant, the process comprising the step of applying a composition comprising a polyene antifungal agent and at least one phosphite containing compound to the plant that does not contain any fruit or potato, wherein the polyene antifungal agent and the at least one phosphite containing compound are present in the composition in an amount that is synergistic against a fungus, and wherein the phosphite containing compound is phosphorous acid or a salt thereof, a (C1-C4) alkyl ester of phosphorous acid or a salt thereof, or a mixture thereof.

2. The process according to claim 1, wherein the polyene antifungal agent is natamycin.

3. The process according to claim 1, wherein the composition further comprises at least one additional compound selected from the group consisting of a sticking agent, a surfactant, a further antifungal compound, a compound to combat insects, nematodes, mites and/or bacteria, a mineral substance, a solvent, a dispersant, an emulsifier, a wetting agent, a stabiliser, an antifoaming agent, a buffering agent, an UV-absorber and an antioxidant.

4. The process according to claim 1, wherein the application of the composition prevents or inhibits fungal growth on or in the plants.

5. The process according to claim 4, wherein the fungus is selected from the group consisting of *Mycosphaerella musicola, Mycosphaerella fijiensis, Fusarium oxysporum, Alternaria solani* and *Alternaria alternate*.

6. The process according to claim 1, wherein the composition is applied to the plants by spraying.

7. A process of protecting or treating a banana or plantain plant or a potato plant against mould growth, the process comprising administering a polyene antifungal agent and at least one phosphite containing compound to the banana or plantain plant or potato plant that does not contain any fruit or potato, wherein the polyene antifungal agent and the at least one phosphite containing compound are administered in an amount that is synergistic against a fungus, and wherein the phosphite containing compound is phosphorous acid or a salt thereof, a (C1-C4) alkyl ester of phosphorous acid or a salt thereof, or a mixture thereof.

8. The process according to claim 1, wherein the phosphite containing compound is a potassium phosphite, sodium phosphite, or ammonium phosphite.

9. The process according claim 1, wherein the phosphite containing compound is aluminum ethyl phosphite, calcium ethyl phosphite, magnesium isopropyl phosphite, magnesium isobutyl phosphite, magnesium sec-butyl phosphite, or aluminum N-butyl phosphite.

10. The process according to claim 1, wherein the ratio of phosphite containing compound to polyene antifungal agent in the composition is between 2:1 to 500:1.

11. The process according to claim 1, wherein the ratio of phosphite containing compound to polyene antifungal agent in the composition is between 3:1 to 300:1.

12. The process according to claim 1, wherein the ratio of phosphite containing compound to polyene antifungal agent in the composition is between 5:1 to 200:1.

13. The process according to claim 1, wherein the polyene antifungal agent is natamycin, nystatin, amphotericin B, aureofungin, filipin, or lucensomycin.

14. The process according to claim 1, wherein the phosphite containing compound is potassium phosphite.

15. The process according to claim 1, wherein the composition comprises 0.005 g/l to 100 g/l of polyene antifungal agent and 0.5 g/l to 1000 g/l of phosphite containing compound.

16. The process according to claim 1, wherein the composition comprises 0.01 g/l to 50 g/l of polyene antifungal agent and 1 g/l to 500 g/l of phosphite containing compound.

17. The process according to claim 1, wherein the composition comprises 0.03 g/l to 3 g/l of polyene antifungal agent and 2 g/l to 200 g/l of phosphite containing compound.

* * * * *